_US005831027A_

United States Patent [19]

McIntosh et al.

[11] Patent Number: 5,831,027

[45] Date of Patent: Nov. 3, 1998

[54] HEAT TREATED BLOOD PLASMA PROTEINS

[75] Inventors: Ronald Vance McIntosh, North Berwick; John Charles Hardy, Edinburgh, both of United Kingdom

[73] Assignee: Common Services Agency, United Kingdom

[21] Appl. No.: 849,498

[22] PCT Filed: Dec. 8, 1995

[86] PCT No.: PCT/GB95/02902

§ 371 Date: Aug. 1, 1997

§ 102(e) Date: Aug. 1, 1997

[87] PCT Pub. No.: WO96/17631

PCT Pub. Date: Jun. 13, 1996

[30] Foreign Application Priority Data

Dec. 8, 1994 [GB] United Kingdom ................... 9424732

[51] Int. Cl.⁶ .............................. A61L 2/04; A61L 25/00; C07K 14/75; C07K 14/755

[52] U.S. Cl. ........................ 530/382; 530/383; 530/421; 530/418

[58] Field of Search .................................. 530/382, 383, 530/418, 421

[56] References Cited

U.S. PATENT DOCUMENTS

| | | | |
|---|---|---|---|
| H1509 | 12/1995 | Eran et al. | 530/383 |
| 4,739,039 | 4/1988 | Vasquez et al. | 530/383 |
| 4,816,251 | 3/1989 | Seelich | 424/101 |
| 5,099,002 | 3/1992 | Rubinstein et al. | 530/381 |
| 5,610,147 | 3/1997 | Seelich et al. | 514/21 |

FOREIGN PATENT DOCUMENTS

| | | |
|---|---|---|
| 0 171 506 | 2/1986 | European Pat. Off. . |
| 0 183 674 | 6/1986 | European Pat. Off. . |
| 0 212 040 | 3/1987 | European Pat. Off. . |
| 84 03628 | 9/1984 | WIPO . |
| 88 08710 | 11/1988 | WIPO . |

*Primary Examiner*—Cecilia J. Tsang
*Assistant Examiner*—Cecilia Wang
*Attorney, Agent, or Firm*—Bell Seltzer Intellectual Property Law Group of Alston & Bird LLP

[57] ABSTRACT

A lyophilized fibrinogen is produced which is subjected to a severe terminal virucidal heat treatment in order to inactivate viruses present, while retaining desirable biological properties. In particular the lyophilized fibrinogen has a solubility in water or other aqueous solution to 40 g/l in less than 20 minutes at 20° C., and a clotting time of less than 10 seconds when exposed to at least 200 U/ml thrombin. The product may be heat treated at 80° C. for 72 hours up to 100° C. for 10 hours depending on formulation and water content. In the production process cryoprecipitate is washed with polyethylene glycol solution at 4 to 10° C. and pH 6.8 to 8 at low ionic strength, prior to two-stage freeze drying.

21 Claims, 2 Drawing Sheets

HEAT TREATED BLOOD PLASMA PROTEINS

This application is a U.S. national stage application of PCT/GB95/02902 filed on Dec. 8, 1995.

TECHNICAL FIELD

The present invention relates to the production of cryoprecipitatable blood plasma proteins, such as fibrinogen, which are capable of being severely heat treated in order to substantially inactivate major blood-borne viruses that may be present; whilst at the same time maintaining the desirable properties of the plasma protein, such as solubility in aqueous solution and functional (e.g. clotting) activity.

BACKGROUND

As is well known, blood plasma contains a series of coagulation factors which contribute to clot formation. Recently, a type of natural glue referred to as fibrin sealant has been prepared utilising certain of these blood coagulation factors. Thus, fibrinogen when combined with thrombin will form fibrin, an insoluble adhesive biological polymer. When Factor XIII is also present, cross-linking of the fibrin occurs which stabilises and strengthens the clot which is formed. The use of fibrinogen and thrombin concentrates in this way represents a major technical advance in surgery (references 1 to 4). Indeed, several fibrin sealant products are available commercially and have been used extensively in a number of European countries. By way of example, patent specifications GB2041942, GB2042556 and WO86/01814 describe various ways of producing fibrin sealant preparations. In practice, fibrin sealant has found a variety of surgical uses including the repair of vascular and anastomoses, repair of soft tissue injuries e.g. of the liver and spleen, and repair of lung lascerations.

The fibrin sealant is generally provided as two separate concentrates of fibrinogen and thrombin respectively, which are mixed shortly prior to use. Clotting of the fibrin sealant can take place relatively rapidly and specialised applicators for applying the fibrin sealant to a wound are disclosed in a number of patent specifications such as EP0037393, EP0315222, EP0156098 and U.S. Pat. No. 4,650,678.

In addition to its use as a component in fibrin sealant, suitable preparations of fibrinogen can also be infused to treat disorders such as hypo-, dys- and afibrinogenaemia.

However, despite the apparent effectiveness of such products, their use in the United Kingdom and the USA has up till now been limited partly because of availability but also because of fears of the transmission of blood-borne viruses by fibrinogen based preparations (reference 5). Typically, each human plasma donation is screened for the following virus markers; hepatitis B surface antigen, antibodies to human immuno deficiency virus (HIV) types 1 and 2, and hepatitis C virus, using validated test methods. Although such screening procedures have contributed greatly to the safety of blood products, there is a residual risk of virus contamination. Therefore a variety of methods for viral inactivation of blood products are known, including the use of detergents and heat treatment. However, these are of varying reliability. Terminal heat treatment of dry product has been widely proposed as a safe and effective method of virus inactivation and is referred to for example in patent specifications EP00944611, PCT/US90/01088, EP0345246, EP0159311 and EP0183674. In terminal heat treatment, the heating is carried out as a last step in the processing thereby eliminating the chances of recontamination.

However, terminal heat treatment has a number of potential disadvantages which detract from the utility of the procedure. Thus, in order to provide a sufficiently high level of virus inactivation, it may be desirable to heat at a temperature of at least 70° C. for 50 to 100 hours. Under such severe heat treatment conditions, the plasma protein is liable to undergo undesirable degradations which may result in reduced biological activity. Furthermore, the solubility of the plasma protein on reconstitution prior to use may be significantly reduced.

A high-yield Factor VIII concentrate suitable for severe terminal heat treatment has been disclosed by one of the present inventors (Reference 10) and this involves particular formulation and lyophilisation steps.

It is an object of the present invention to provide for the production of a cryoprecipitatable plasma protein, particularly fibrinogen, which is capable of viral inactivation via severe (generally terminal) heat treatment.

SUMMARY OF THE INVENTION

Generally speaking, the present invention lies in the use of a combination of treatment measures to produce a lyophilised blood plasma protein, such as fibrinogen, which has appropriate solubility characteristics and effective biological clotting activity, yet at the same time is able to have been heat treated under relatively severe heat treatment conditions to ensure substantially complete viral inactivation.

Whilst the present invention lies in a combination of measures, a particularly important feature is the use of an aqueous solution of a non-polar polymeric material (such as polyethylene glycol) or other material as described herein, in a suitable concentration to wash protein which has been cryoprecipitated (or alternatively to precipitate the protein in the presence of the non-polar polymeric material) such as to remove heat-degradable plasma proteins therefrom, prior to lyophilisation and viricidal heat treatment.

Thus, a first aspect of the present invention provides a lyophilised fibrinogen which has been heat treated (preferably terminally heat treated) to substantially inactivate any viruses present and so as to be non-infective, and which has (a) a solubility in water or other pharmaceutically acceptable aqueous solution to 40 g/l fibrinogen in less than 20 minutes at 20° C.; and (b) a clotting time of less than 10 seconds when exposed to at least 200 U/ml thrombin.

Thrombin activity is defined with reference to human alpha-thrombin standard 89/588 of the UK National Institute of Biological Standards and Control.

Thus, the lyophilised fibrinogen has good solubility in an aqueous vehicle to enable reconstitution prior to use, and also good residual clotting activity measured as the clotting time, whilst at the same time having been heat treated to substantially inactivate any viruses present by means of a relatively severe heat treatment regime so as to ensure good safety as regards viral transmission.

The fibrinogen is lyophilised (i.e. freeze dried) so that the material may be stored in a solid dry state to ensure good long term storage stability. On the other hand, the fibrinogen must be made up into an aqueous solution prior to use. Clearly, in order to be practically useful, the fibrinogen must be capable of redissolution in water or other pharmaceutically acceptable aqueous vehicle in a reasonably short time. However, fibrinogen is a material of relatively low inherent solubility and any processing thereof tends to render the product even less soluble. It is therefore important that in the process of the present invention, suitable solubility characteristics are maintained as far as is practical. The lyophilised fibrinogen preparation of the present invention has a solubility in water to a desired concentration of 40 g/l in less than 20 minutes at 20° C. Generally, the product of the present invention can be fully dissolved under these conditions in less than 10 minutes, and typically the reconstitution time is in the range 5 to 10 minutes. This satisfies a proposed European Pharmacopoeia Commission (PA/PH/Exp.6B/T (91)2) dissolution time requirement of within 20 minutes. In our experience, it is unique to be able to attain such solubility characteristics after a severe viricidal terminal heat treatment as described herein.

Whilst a concentration of 40 g/l has been mentioned above in connection with a rate of dissolution, in fact the maximum concentration attainable is higher than this (e.g. 50 g/l) and amounts of up to 60 g/l can be dissolved.

It is also important that the lyophilised fibrinogen of the present invention should have a good clotting time which is defined as being less than 10 seconds to form a clot when exposed to at least 200 U/ml thrombin. Since the speed of clotting is proportional to the amount of active fibrinogen present, this criterion is an effective practical measure of residual clotting activity.

A further factor involved in the assessment of clottability is the presence of Factor XIII, which strengthens the clot formed by cross-linking the fibrin fibrils and mitigates against premature dissolution of the clot. It is recognised that certain amounts of Factor XIII have to be present in order to provide a clot of long term stability. We have found that amounts of Factor XIII in the range 0.14 to 0.64 U per mg of the fibrinogen give clots of good stability. One U is defined as the amount of Factor XIII present in 1 ml of normal human plasma. Variations of Factor XIII concentration within this range do not lead to any significant difference in strength of the clot. In fact amounts of Factor XIII less than 0.14 U/mg fibrinogen may also be useful provided that rate of stable clot formation is not unduly slow. The clot stability, and indirectly the Factor XIII concentration, may be assessed by means of a urea solubility test as outlined in detail herein. A clot of suitable stability is obtained if the clot remains substantially insoluble in 6M urea when stored overnight. This is assessed in terms that less than 10% of the clottable protein dissolves in 6M urea, generally less than 5% dissolves and typically 0.5 to 2% of the clot dissolves.

Whilst stable clot formation (and thus the presence of Factor XIII) is important where the lyophilised fibrinogen is to be used to produce fibrin sealant, in other uses the presence of Factor XIII is not essential. Thus, where the fibrinogen is to be administered to deal with a fibrinogen deficiency in a patient (e.g. hypo-, dys- or afibrinogenaemia) there is usually no requirement for the presence of Factor XIII.

In order to be acceptable, the lyophilised fibrinogen must have been substantially virally inactivated to an acceptable safe level. It is known that different viruses may be heat-effected to different extents. However, it is important that inter alia hepatitis A, B and C viruses and HIV viruses are substantially inactivated in order to provide for product safety; and reference herein to substantial inactivation of any viruses present refers to substantial inactivation of at least these virus types. In laboratory tests using viruses of these types, viral titre reductions of at least $1 \times 10^2$ may be achieved. The present lyophilised fibrinogen is capable of heat treatment more severely than previously available preparations.

The severity of heat treatment is a function both of temperature and time and the two are inversely related. We have shown with regard to other plasma proteins such as Factor VIII, that a terminal heat treatment at 80° C. for 72 hours gives a product a proven safety. Heat treated Factor VIII preparations treated in this manner have an excellent safety record. The present lyophilised fibrinogen is also capable of being treated under such standardised heat treatment conditions. However, it is capable of even more severe heat treatment conditions and may, for example, be heated at 90° C. up to 100° C. for 10 hours or longer, depending upon the product formulation and residual water content. The relationship between efficacy of heat treatment and residual water content is known in the art. In contrast, other heat treatments disclosed in the art, such as 60° C. for 10 hours are in our opinion probably not fully viricidal and thus represent a potential safety hazard. In the present invention, viral inactivation has been measured employing Semliki Forest virus which is similar in characteristics to hepatitis C virus. Tests have also been done showing reduction in HIV virus. Viral titre reductions of at least $1 \times 10^2$ and up to $1 \times 10^3$ to $1 \times 10^6$ or more may be achieved.

It has also been found that the severe heat inactivation may be carried out on lyophilised fibrinogen preparations which have also undergone a solvent detergent viral inactivation step, thereby allowing even more effective overall inactivation to be achieved.

A second aspect of the present invention relates to a process for the production of a cryoprecipitatable blood plasma protein, such as fibrinogen, which has undergone viricidal heat treatment, which comprises;

(i) precipitating the cryoprecipitatable protein or washing the cryoprecipitatable protein with an aqueous solution comprising a non-polar polymeric material, such as to substantially remove heat-degradable plasma proteins therefrom;

(ii) lyophilising the cryoprecipitatable protein; and (iii) undertaking a viricidal heat treatment of the lyophilised cryoprecipitatable protein, so as to render it non-infective.

The term "cryoprecipitatable protein" is well understood in the art and refers to the product of a well known plasma protein separation technique wherein the blood plasma is frozen, for example to −40° C., and left for a period of time. The temperature is allowed to rise, for example to −1° C. to +2° C. which results in some partial thawing of the plasma leaving behind a solid material referred to as cryoprecipitate. The supernatant is removed and the cryoprecipitate further processed. The cryoprecipitate is a mixture of materials but includes predominantly fibrinogen, fibronectin, Factor VIII and Factor XIII. It is an important feature of the present invention that this cryoprecipitate is washed in order to substantially remove plasma proteins which might be heat-degraded during the subsequent viricidal heat treatment.

In an alternative form of preparation of fibrinogen, the cryoprecipitate is produced under somewhat different washing conditions and the fibrinogen is recovered from the supernatant material by precipitation with a suitable concentration of the non-polar polymeric material.

The non-polar polymeric material used to wash the cryoprecipitatable protein is preferably a polyethylene glycol (typically of molecular weight 600 to 6,000) but might also be a polyvinylpyrrolidone, a hydroxyethyl starch, or a suitable cellulose material. Sugars should not be included in the wash solution since they tend to promote dissolution of fibrinogen. The amount of polyethylene glycol employed will depend on the particular grade and molecular weight employed but it is found that a concentration of 4% by weight polyethylene glycol 4000 in aqueous solution will maintain fibrinogen in the solid phase whilst allowing removal of undesired plasma proteins. Generally speaking, the amount of polyethylene glycol will be in the range 3% to 3 weight/volume. Generally speaking, the non-polar polymeric material is non-ionic and of relatively high molecular weight. Polyhydroxy materials are particularly useful. Such materials are able to replace water in the hydration shell of the fibrinogen and therefore exert a dewatering effect. By way of contrast, prior art proposals have involved washing with salt-containing buffer solutions, but these do not exert the same dewatering effect and very high molar concentrations of salt would be required in order to exert a dewatering effect of the type encountered by the polyethylene glycol employed in the present invention. High salt concentrations are undesirable in that they leave residues which have to be removed prior to formulation of the product for subsequent lyophilisation. Thus, whilst the use of polyethylene glycol in the processing of blood plasma is not unknown, the present invention has identified washing with polyethylene glycol (or other non-polar polymeric materials) as being particularly useful in the process of the present invention.

Generally, washing is carried out at a temperature in the range 4° C. to 10° C. (and possibly up to room temperature depending on the amount of non-polar polymeric material in the wash solution) and this temperature range is not as critical as washing procedures described in the prior art, thereby contributing to the controllability of the present process.

The pH of the washing solution is generally in the range 6.8 to 8. In contrast, the prior art proposals have generally required washing at more acid pH which can be disadvantageous to the ultimate quality of the fibrinogen produced.

Furthermore, washing according to the present invention can be carried out at low ionic strengths. This again simplifies reformulation of the fibrinogen for subsequent lyophilisation. In contrast, prior art washed solutions have generally been of higher ionic strengths in order to prevent dissolving of the fibrinogen.

The washed cryoprecipitate is then formulated into a final formulation buffer ready for lyophilisation. The formulation may include carbohydrates, such as sucrose, and amino acids, such as argenine, to protect the formulation during freezing and to stabilise during subsequent heat treatment. Salt may be included in the formulation to assist in redissolution of the fibrinogen.

Freeze drying is preferably carried out employing a two-stage freezing procedure, such as described in our work in Thrombosis Haemostasis (1987) 58 306 (Reference 10). The two-stage freezing procedure involves supercooling to produce a frozen solid comprising a large number of small crystals. The temperature is eventually reduced to −40° to −50° C. to ensure that freezing is complete before primary freeze drying occurs under reduced pressure, typically 0.01 Mbar to 1 Mbar. This may be followed by secondary drying designed to reduce the residual water content of the lyophilised product to provide long term stability and to provide a residual water content optimised for effective viricidal heat treatment. Generally, a residual water content in the range 0.8 to 2.5% w/w is preferred. A secondary drying temperature of 15° C. to 40° C. may be used for 10 to 48 hours.

The lyophilised plasma protein may then be subjected to a viricidal heat treatment as discussed above and a standard heat treatment regime is 80° C. for 72 hours, although higher temperatures can also be used. Prior art products are unable to retain desirable functional and/or solubility characteristics after such severe heat treatment conditions.

A particular benefit of the present invention lies in the use of a terminal heat treatment. Thus, the lyophilised protein may be sealed in a vial and heat-treated, and is then ready for storage and use. The sealed vial is heat-treated ant is not opened again until the protein is used. Recontamination of the protein is thus avoided.

The lyophilised plasma protein produced has good solubility in water (i.e. dissolves within 20 minutes) and retains greater than 80%, usually greater than 90% and often substantially 100% of its original clotting activity. Furthermore, the product is safe and suitable for use in fibrin sealant formulations.

BRIEF DESCRIPTION OF THE DRAWINGS

Some of the features and advantages of the invention having been described, others will become apparent from the detailed description which follows, and from the accompanying drawings, in which.

DETAILED DESCRIPTION OF PREFERRED EMBODIMENTS

Embodiments of the present invention will now be described by way of example only.

EXAMPLES (MANUFACTURING METHODS)

Figure 1:
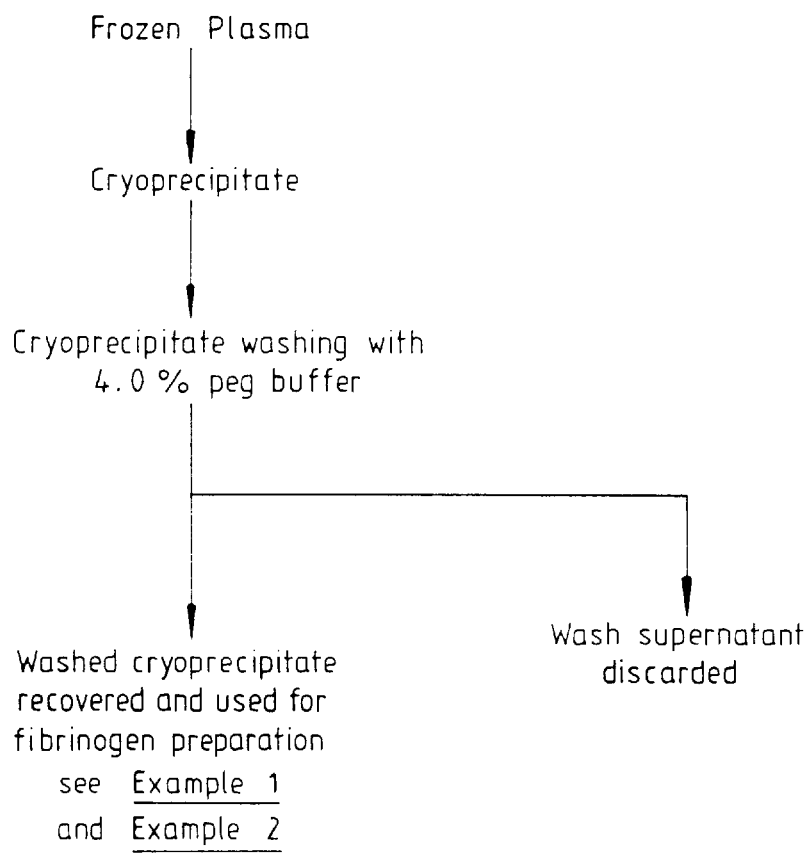
FIG. 1 is a flow chart illustrating the preparation of fibrinogen concentrate from plasma not required for Factor VIII (FVIII) production.

The fibrinogen concentrate is manufactured from cryoprecipitate which is prepared by freezing and thawing plasma. Cryoprecipitate can also be used to prepare another product—Factor VIII. When the plasma is not suitable for the manufacture of FVIII then the cryoprecipitate from that plasma can be used directly for fibrinogen production. When the plasma has been collected for FVIII production the cryoprecipitate will be processed to FVIII. However, fibrinogen can also be prepared as a by-product of the processing of FVIII from cryoprecipitate. These two general manufacturing approaches are outlined in FIGS. 1 and 2 respectively which also refer to the more detailed examples of each of the different methods given below.

In addition to the text below tables of the process operations for each of the examples of the different manufacturing methods are also appended.

Example 1 (directly from cryoprecipitate)

1000 Kg fresh frozen or time-expired plasma, which has been held frozen at −40° C., is placed at −10° C. to −20° C. overnight. The following morning the plasma is removed from the plasma packs and crushed allowing the temperature to rise to −1° C. to +2° C. The thawed plasma is centrifuged at zero to +2° C. to collect the cryoprecipitate.

The cryoprecipitate is isolated and washed by mixing at 4° C.–10° C. with 20–50 mM Tris pH7.0 buffer containing 3% to 20% w/v PEG 4000, at a ratio of 1 part cryoprecipitate, to 2 to 10 volumes buffer, for ten minutes. The mixture is centrifuged at 4° to 10° C. to recover the washed cryoprecipitate which contains the majority of the fibrinogen, fibronectin and FXIII in the cryoprecipitate but is greatly depleted in most other plasma proteins especially albumin, plasminogen, FII and immunoglobulin. Their removal by this simple step is preferred to ensure satisfactory resolution time and product function after heat treatment.

The washed cryoprecipitate may be redissolved at 20° to 25° C. directly into the final formulation buffer. This buffer contains Tris at a concentration of 2–50 mM/L (typically 20 mM/L) Tri sodium citrate (5–80 mM/L; typically 40 mM/L) and sucrose (0.5 to 5.0% w/v typically 3% w/v) at a final pH of 6.8 to 7.6. Since little or no solids remain, the fibrinogen concentration is adjusted to 10 to 15 g/l and the product filtered aseptically. Dispensing into final containers (vials) may vary so that different dose sizes may be produced. For example the containers may be 30 ml vials with 8 ml to 20 ml of product per vial, 50 ml vials with 10 ml to 40 ml per vial, or 250 ml vials containing 40 ml to 150 ml. Freezing and lyophilisation is now necessary.

The freezing of the product is performed in such a way as to produce a uniform fine crystal lattice which is preferred for preserving structure and function of the fibrinogen during subsequent lyophilisation and heat treatment.

The volume of product dispensed and the vial used dictate which freezing conditions must be employed. The temperature of the freeze-drier shelf may be −20° C. to +20° C. on loading and the time at this shelf temperature may be 20 minutes to 2 hours. The shelf temperature is then reduced and when the temperature of the product reaches −40° C. and preferably −50° C. a delay of 2 hours to 24 hours is required to ensure complete freezing of all the product contents before primary drying commences.

Primary drying conditions are also dictated by the volume of product dispensed into each vial and by the vial size. During primary drying, the product temperature must preferably be below −30° C. so that ice sublimation occurs without localised melting of the frozen plug structure. This stage may require 50 hours to 150 hours for completion depending on size of vial and fill volume. The chamber pressure during primary drying may be 0.01 mbar to 1 mbar.

Secondary drying conditions are designed to reduce the residual water content of the lyophilised product so that long-term stability of the product will be enhanced. It has been identified that greater than 0.8% w/w residual water content is preferred for virus inactivation during subsequent heat treatment. It has further been identified that greater than 2.5% w/w water content results in loss of product function (as measured by solubility time and clotting ability) over heat-treatment at 80° C. for 72 hours. The secondary drying conditions are therefore adjusted to ensure that residual water content remains within the desired range required for the final heat treatment conditions. A product temperature of 15° C. to 40° C. may be used for 10–48 hours, depending on vial size, product volume and desired final residual water content.

The lyophilised Fibrinogen preparation may be heat treated at 70° C. to 100° C. for up to 96 hours. Solubility time in water of material so heated is good (10 to 20 minutes) and product function is preserved. Clotting time was less than 10 seconds when exposed to 200 U/ml thrombin and the clot was stable with typically only 0.5 to 2.0% of the clottable protein being soluble in 6M urea.

Fibrinogen preparation manufactured as described above was contaminated with viruses in the laboratory before freezing, lyophilisation and heat treatment at 80° C. for 72 hours. When assaying for virus activity it was evident that considerable infectivity had been lost over heat treatment. Semliki Forest Virus showed a reduction of >5.2 log (no activity remains) at a RWC of 1.14%. Human Immunodeficiency Virus type 1 showed a reduction of >4.3 log at 0.76% residual water content.

Example 2

A human fibrinogen preparation may be manufactured as in Example 1. In order to enhance solubility time and improve filtration, a differential extraction of the washed cryoprecipitate is included. This step results in a variable amount of the washed cryoprecipitate solids remaining insoluble which can be compacted and removed by a centrifugation step. The amount of insoluble material may vary between batches and is dependent upon cryoprecipitate quality and source. The extraction is performed at low ionic strength and at 18°–30° C. The centrifugation step is preferred at a lower temperature (4°–18° C.) to allow a more compact precipitate to form. The ratio of buffer to washed cryoprecipitate is typically between 2 volumes and 10 volumes of 20 mM Tris pH7.5 to 1 part solids. The supernatant may be processed further as in Example 1. Freeze dried heat-treated fibrinogen prepared in this manner redissolved in 5 to 10 mins and showed the same clotting time and clot stability as in Example 1.

Example 3

Human Fibrinogen Preparation may be manufactured as in Examples 1 and 2. In order to enhance the rate of resolution after heat treatment and allow an increase in the temperature of the heat treatment of the final product the sucrose stabilisers may be replaced wholly or in part by the amino acid L-arginine. A concentration of 50 mM is suitable as an entire replacement or 5–25mM in addition to the sucrose at 1 to 3% wt/v. Freeze dried heat-treated fibrinogen prepared in this manner exhibited the same solubility, clotting time and clot stability as in Example 2.

Example 4 (by-product of FVIII production)

Cryoprecipitate from fresh frozen plasma which is suitable for manufacture of FVIII concentrate is washed in a PEG containing (0.1 to 4% PEG 4000) buffer such as Tris (5–50mM) at a suitable pH (6.5 to 8.0) and at a low temperature (0° to 150° C.). The wash buffer may additionally contain excipients such as heparin (0.1 to 20 U/ml), Tri sodium citrate (1.0 to 100 mM) and calcium chloride (0.5 to 10 mM). The washing ratio may range from 1:1 to 1:10 of cryoprecipitate to wash buffer (preferably 3.5 to 5.0:1) and temperature may range from 0° C. to 15° C. (preferably 4° C.).

The supernatant of this washing process contains an appreciable quantity of fibrinogen of high quality. This fibrinogen is harvested by increasing the PEG concentration by up to 10% w/v but preferably to 3.5 to 4% w/v at 0°–10° C. and collecting the precipitate by centrifugation.

The fibrinogen-rich precipitate so collected may be processed immediately or stored frozen (lower than −20° C.) for later processing (up to 1 year).

The freshly prepared or frozen fibrinogen precipitate may be processed to a lyophilised heat treated fibrinogen preparation as in Examples 1 to 3. Fibrinogen prepared in this manner redissolved in 5 minutes and showed the same clotting time and clot stability as in Examples 1 to 3.

Example 5

Figure 2:
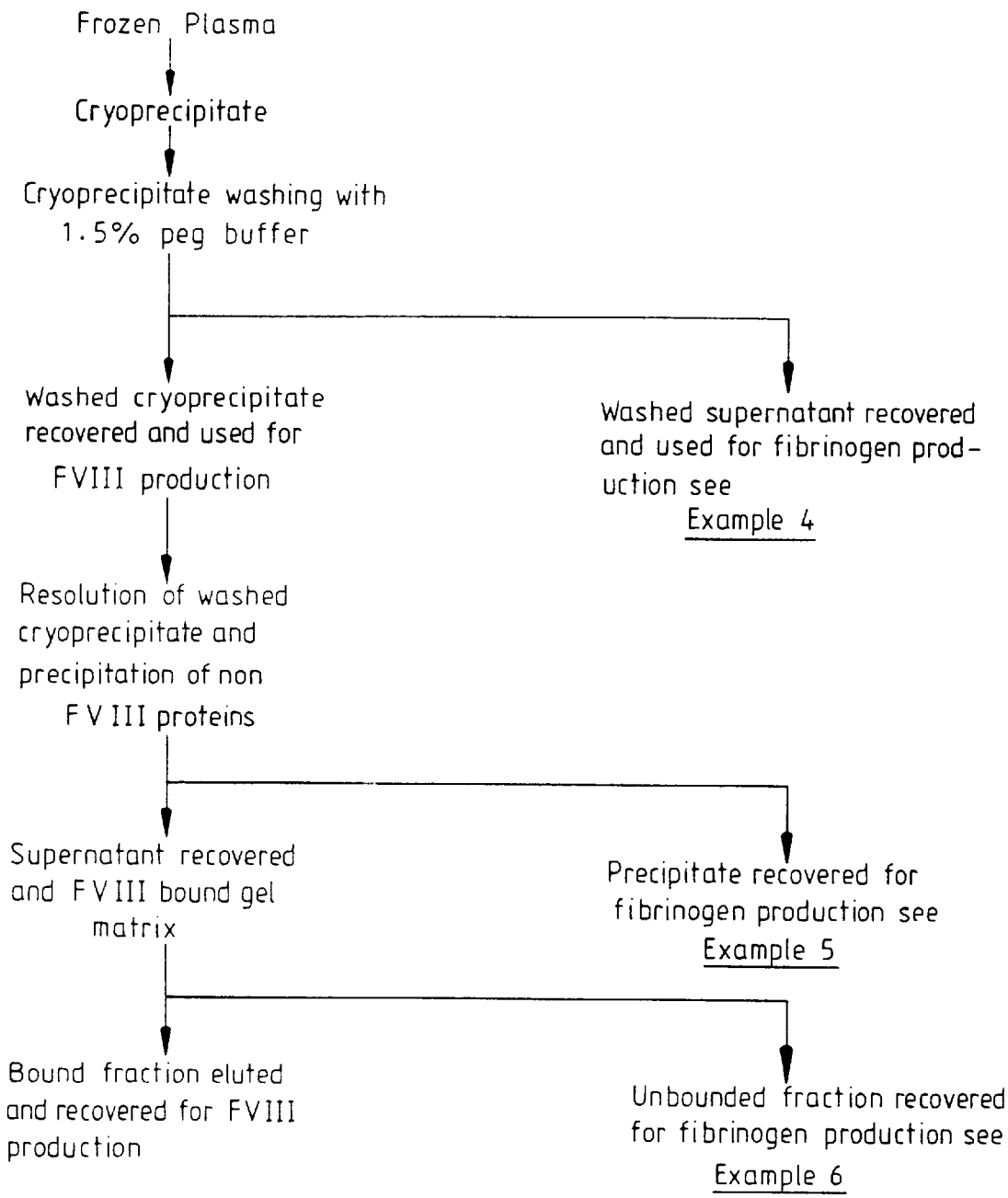
FIG. 2 is a flow chart illustrating the preparation of fibrinogen concentrate from plasma also used for Factor VIII (FVIII) production.

Cryoprecipitate from fresh frozen plasma which is suitable for manufacture of FVIII concentrate is washed as in FIG. 2 and the solids dissolved extracted in a suitable buffer eg. Tris at a suitable pH eg. 6.0 to 8.0. After solubilising or extracting the FVIII from the washed cryoprecipitate it is possible to purify the FVIII and remove less soluble proteins such as fibrinogen and fibronectin by precipitation using for example metal ions such as zinc as chloride or sulphate, (up to 50 mM) in conjunction with heparin (up to 25 U/ml) if required and an absorptive agent eg. aluminium hydroxide (up to 20% w/v).

The solids from this precipitation step are fibrinogen rich. They may be extracted by redissolving in a suitable buffer (5 to 50 mM Tris pH7.5, 5 to 100 mM trisodium citrate) and removing the insoluble material (mainly aluminium hydroxide) by centrifugation. The fibrinogen in the supernatant may be harvested by PEG precipitation (3 to 10% w/v) and the resulting fibrinogen precipitate processed to a lyophilised and heat treated fibrinogen preparation as in FIGS. 1 to 3. Fibrinogen prepared in this manner had the same solubility, clotting time and clot stability as in Example 4.

Example 6

The supernatant of the metal ion precipitation step in Example 5 is not only rich in FVIII but also fibrinogen. The FVIII may be bound to an affinity or ion exchange matrix either before or after treatment with a solvent (eg. TNBP at 0.1 to 2% v/v) and a detergent (eg. Tween 80 at 0.2 to 5% v/v) and the fibrinogen recovered from the unbound material.

The fibrinogen may be recovered from this unbound fraction by precipitation using PEG 4000 (2 to 10% w/v). If the fraction contains solvent and detergent several sequential PEG precipitation steps may be required (three or more) in order to reduce the level of contamination by these agents to an acceptable level. At each stage the precipitated fibrinogen must be solubilised in a suitable buffer (eg. 5 to 50 mM Tris pH7.5, 5 to 100 mM trisodium citrate, 0.1% to 2.5% w/v sodium chloride). The final precipitate may be processed to a lyophilised and heat treated fibrinogen preparation as in Examples 1 to 3 with the same solubility, clotting time and clot stability as in Example 4.

The clotting activity and viral deactivation of the products of Examples 2 to 5 was similar to that of Example 1.

This Example also demonstrates that these methods for preparing terminally heat treated fibrinogen can be combined with solvent detergent treatment to give a product with two very effective and complementary virus inactivation steps.

TEST 1
CLOT STABILITY ASSAY OF FIBRINOGEN
INTRODUCTION

Fibrin Sealant is a product which has been developed for use in various surgical procedures. It consists basically of a preparation of fibrinogen and a preparation of thrombin which, once in solution, are brought together to form fibrin which acts as a sealant at wound sites minimising seepage from the wound area and which allows normal wound healing.

To function properly the fibrin clot must have a minimum degree of cross-linking and this describes a method whereby clot stability, i.e. ability to resist re-solution by urea, is assayed. This provides an indirect but functional measure of the degree of cross-linking (by FXIIIa activity) in the clot.

REAGENTS

The following reagents are required for the assay
(a) A 0.9% (w/v) aqueous solution of sodium chloride (9 g/l).
(b) A 6M aqueous solution of urea (360 g/l).
(c) Thrombin (available from Armour Pharmaceuticals) dissolved in 40 mM calcium chloride to give the required concentration of 200 U/ml.
(d) A 20 mM TRIS solution pH 7.50.

PROCEDURE

Dissolve the contends of the vials of lyophilised fibrinogen in 5 ml 20 mM TRIS pH 7.50, at room temperature. The preparations should be in solution within 20 minutes. When the samples are dissolved, prepare a solution of thrombin in 40 mM calcium chloride to a final concentration of 200 U/ml.

using a suitable apparatus prepare 0.5 ml clots (total volume) as follows.

use new sterile 1 ml syringes for each set of samples. Draw 0.25 ml thrombin solution into one syringe and 0.25 ml fibrinogen solution into the other for each clot which is to be formed. Simultaneously dispense and mix equal volumes of both solutions avoiding bubble formation.

Allow the samples to stand for 1 hour at room temperature, then add one ml of 0.9% sodium chloride to one set of duplicates and one ml 6M urea to the other set. Cap the tubes and allow them to stand overnight at room temperature.

Next day, decant the supernatant from the tubes into fresh clean tubes and examine the clots for signs of dissolution.

In order to pass this test, the protein concentration of the saline and urea supernatants (measured using a suitable method e.g. as in reference 6) should be less than 0.4 g/l.

Take the mean of the protein concentration in each pair of saline and urea supernatants corresponding to each fibrinogen sample. Subtract the mean saline value from the mean urea value=X mg. Find the concentration of fibrinogen in each sample by means of the current QC fibrinogen concentration assay =Z mg/ml. There is 0.25 ml of this in each clot which corresponds to 0.25 ml×Z mg/ml=A mg.

The percentage of fibrin solubilised by urea in each sample is thus:

$$X/A \times 100\%$$

If the percentage is greater than 10%, the sample has failed the clot stability test.

TEST 2 (Clot Strength Assay—Rat Skin Incision test)

The use of the assay described in Test 1 was validated in conjunction with an in vivo model.

Briefly, standard dorsal skin incisions in adult male Wistar rats were closed with tape alone or with Fibrin Sealant and tape. Different formulations of Fibrin Sealant to contain various concentrations of fibrinogen, FXIII and thrombin were used to close the incisions.

After a suitable period the animals were killed and the wounds excised. The excised wounds were then tested mechanically and the stress, strain, elasticity and work done to rupture the wounds was measured. In this way it could be demonstrated that there were optimum fibrinogen (approximately 39 g/l) and thrombin (200–500 U/ml) concentrations which resulted in healed wounds with significantly increased stress, energy absorption and elasticity values compared to those treated with lower but also higher fibrinogen concentrations. It could also be shown that under these conditions there was a FXIII requirement of >0.14 U/mg fibrinogen.

It is not practical to perform in vivo functional tests on each batch of Fibrin Sealant prior to clinical use. Therefore it was necessary to develop and validate a laboratory assay of clot strength to ensure an adequate degree of cross-linking of the fibrin fibrils in the clots. This was done by carrying out the clot solubility assay on Fibrin Sealant prepared using various combinations of fibrinogen, FXIII and thrombin similar to those used in the Rat Skin Incision Test. In this way it could be determined that for less than 10% of the clottable protein to be soluble in 6M urea required the fibrinogen preparation to have a FXIII content of greater than 0.25 U/mg of fibrinogen which is significantly higher than the 0.14 U/mg required for wound healing in the Rat Skin Incision test.

TEST 3
Virus Inactivation in the Freeze Dried Human Fibrinogen Preparation during Heat Treatment at 80° C. for 72 hours.

The human fibrinogen used in the virus inactivation studies was prepared from material sampled from full scale production batches prepared in a manner similar to that described earlier.

Viruses and Cell Lines

Semliki Forest virus (SLFV) was originally obtained from Prof. Bourke, Warwick university and was grown and assayed in Vero cells using the cytopathic effect for scoring of positive wells and calculating titres by the method of Reed and Muench (Reference 7), expressed in tissue culture infective doses (TC1D50) per ml of inoculant.

HIV-1 strain RF, was originally obtained from Chester Beatty Laboratories. The HIV-1 virus was grown in H9-NIH cells and assayed in the human lymphoblastoid cell line C8166 using a combination of syncytial formation and a p24 HIV-1 antigen assay. The HIV-1 titres were expressed as in vitro infectious units (IVIu) per ml of test sample.

Sampling and Experimental Design

All virus inactivation measurements were carried out on up to four samples each from duplicate, separate unheated or heat treated vials.

In each experiment, samples were taken before freeze drying and before heat treatment as well as at different time points during the heat treatment process. In this way any loss of virus activity on freeze drying can be accounted for and the figures quoted here are for virus inactivation during heat treatment only. The level of inactivation is presented as a reduction index (RI) and expressed as $\log_{10}$ R1 which is derived as follows:

$$\text{Log}_{10} \frac{\text{Pre-heat treatment titre}}{\text{Post-heat treatment titre}} = \text{Log}_{10} R1$$

Also, by measuring the levels of inactivation at time points during the heat treatment as well as on completion of the heating period it could be determined whether or not the inactivation data were internally consistent, giving further assurance to the overall figure. The experiments on HIV inactivation also included parallel samples containing one of the model viruses (SLFV) as an internal control.

The residual water content of the human fibrinogen preparations used in the virus inactivation experiments was determined in parallel non-inoculated samples.

Model Virus Inactivation Data

SLFV is a Togavirus, belonging to the same family as Hepatitis C, although this family has now been subdivided into Togaviruses and Flaviviruses. It is commonly used as a model for the inactivation of Hepatitis C virus. A summary of the SLFV inactivation data is presented in Table 1. These results show a total inactivation of >5.2 $\log_{10}$ over the 72 hour heating period with over 4.8 $\log_{10}$ inactivated in the first 24 hours.

We conclude that heat treatment of the freeze dried fibrinogen preparation at 80° C. inactivates a relevant model virus.

HIV-1 Inactivation Data

The results of a study of HIV-1 inactivation during the heat treatment of the freeze dried human fibrinogen component of the kit are shown in Table 2. To increase the sensitivity of the HIV assay, analysis was also carried out with the sample volume increased from the normal 1.0 ml (2×0.5 ml) to 40 ml (80×0.5 ml). As Table 2 shows, over 72 hours at 80° C. a total figure of >4.8 $\log_{10}$ reduction in HIV-1 titre was obtained using 0.5 ml samples and a figure of 6.1 to $\log_{10}$ using the larger 40 ml total assay volume.

We conclude that heat treatment of the freeze dried fibrinogen preparation at 80° C. for 72 hours inactivates HIV-1.

A Comparison of Virus Inactivation During The Heat Treatment of The Human Fibrinogen Preparation and The SNBTS FVIII Product Z8.

The virus inactivation data for the heat treatment of the freeze dried human fibrinogen preparation compare favourably with previous data observed during similar heat treatment of the freeze dried Scottish National Blood Transfusion Service (SNBTS) FVIII product Z8.

The SNBTS FVIII product Z8 has shown levels of SLFV inactivation of 5.5±0.9 $\log_{10}$ (n=4) on heat treatment at 80° C. for 72 hours and the human fibrinogen preparation in this study has shown a figure of ≧5.2 $\log_{10}$ reduction during the same heat treatment.

The measured level of HIV-1 inactivation during heat treatment of 72 hours at 80° C. of the human fibrinogen preparation (6.1 $\log_{10}$) is within the range of 5.2 to 7.3 $\log_{10}$ which we have observed on 72 hours/80° C. heat treatment of SNBTS FVIII Z8.

In conclusion it can be said that the levels of virus inactivation seen during the heat treatment at 80° C. for 72 hours of the Human Fibrinogen preparation for use in the Fibrin Sealant kit are similar to and comparable with the levels of virus inactivation seen in the SNBTS FVIII product Z8 which has an outstanding clinical safety record (reference 8), as do other severe terminally heat treated coagulation factor products (reference 9).

TABLE 1

MODEL VIRUS INACTIVATION DURING HEAT TREATMENT OF THE HUMAN FIBRINOGEN.

| VIRUS | SAMPLE | VIRUS TITRE $\text{LOG}_{10}\text{TCID50/ML}$ | VIRUS REDUCTION INDEX $\text{LOG}_{10}$ |
|---|---|---|---|
| SLVF | Pre-freeze drying | 5.2 | — |
|  | Post-freeze drying | 4.7 | 0 |
|  | Post 8 h 80° C. heat treatment | 1.5 | 3.2 |
|  | Post 24 h 80° C. heat treatment | −0.1 | 4.8 |
|  | Post 48 h 80° C. heat treatment | −0.3 | 5.0 |
|  | Post 72 h 80° C. heat treatment | ≦−0.5 | ≧5.2 |

TABLE 2

| SAMPLE DESCRIPTION | HIV TITRE (IVIu/ 0.5 ml) | HIV TITRE (IVIu/ 40 ml) | HIV TITRE $\text{LOG}_{10}$ (IVIu/ 40 ml) | REDUCTION IN HIV TITRE ($\text{LOG}_{10}$) |
|---|---|---|---|---|
| Post Freeze Drying | $10^{4.5}$ | $10^{6.4}$ | 6.4 | — |
| Post 24 h 80° C. Heat Treatment | $10^{0.0}$ | $10^{1.9}$ | 1.9 | 4.5 |
| Post 48 h 80° C. Heat Treatment | $10^{0.3}$ | $10^{1.6}$ | 1.6 | 4.8 |
| Post 72 h 80° C. Heat Treatment | — | $10^{0.3}$ | 0.3 | 6.1 |

REFERENCES

1. Borst H. C., Haverich A., Walterbusch G. and Maatz W. Fibrin Adhesive: an important haemostatic adjunct in cardiovascular operations. Journal of Thoracic and Cardiovascular surgery. 84, 548–553 (1982).
2. Scheele J., Gentsch H. H and Matheson E. Splenic repair by fibrin tissue adhesive and collagen fleece. Surgery; 95, 6–13 (1984).
3. Brands W., Mennichen C. and Beck M. Preservation of the ruptured spleen by gluing with highly concentrated human fibrinogen: Experimental and clinical results. World Journal of Surgery; 6, 366–368 (1982).

4. Mersner H., Struch E., Schmidt-Habelman P. and Sebering F. Fibrin Seal application: Clinical experience. Thoracic and Cardiovascular surgery; 30, 232–233 (1982).
5. Revocation of Fibrinogen Licences: FDA Drug Bulletin; 8, 15 (1978).
6. Rizza C, et al. Confirmation of viral safety of dry heat treated FVIII concentrate prepared by BPL. Br. J. Haematol. 84, 269–272 (1993).
7. Reed L. J. Muench H. A simple method of estimating fifty percent and points. AM. Hyg. 27, 493–497 (1938).
8. Bennet, et al. (1993). Study of viral safety of Scottish National Blood Transfusion Service Factor VIII and Factor IX Concentrate. Transfusion Medicine 3, 295–298.
9. Bradford M. B. A rapid sensitive method for the quantitation of microgram quantities of protein utilizing the principle of protein-dye binding. Anal. Biochem. 72, 248–254 (1976).
10. McIntosh R. V. et al. A high yield Factor VIII concentrate suitable for advanced heat treatment, Thrombosis Haemostasis (58, 306 (1987).

We claim:

1. Lyophilised fibrinogen which has been heat treated to substantially inactivate any viruses present and so as to be non-infective, and which has
   (a) a solubility in water or other pharmaceutically acceptable aqueous solution to 40 g/l in less than 20 minutes at 20° C.; and
   (b) a clotting time of less than 10 seconds when exposed to at least 200 U/ml thrombin.

2. Fibrinogen according to claim 1 which when exposed to said thrombin results in the formation of a stable clot.

3. Fibrinogen according to claim 2 wherein the stability of the clot is such that less than 10% of the clotted protein is soluble in a 6M urea solution when left overnight at room temperature.

4. Fibrinogen according to claim 2 which comprises Factor XIII in an amount of at least 0.14 U per mg of fibrinogen.

5. Fibrinogen according to claim 1 which further comprises residue of solvent detergent from a solvent detergent viral inactivation step.

6. Fibrinogen according to claim 1 having a solubility of 50 to 60 g/l in water or other pharmaceutically acceptable aqueous solution at 20° C.

7. Fibrinogen according to claim 1 having a solubility to 40 g/l in 5 to 10 minutes at 20° C.

8. Fibrinogen according to claim 1 which has been heat-treated at least at a severity of 80° C. for 72 hours.

9. Fibrinogen according to claim 1 which has been heat-treated at least at a severity of 90° C. for 10 hours.

10. A process for the production of a cryoprecipitatable blood plasma protein, which has undergone viricidal heat treatment, which comprises;
    (i) substantially removing heat-degradable plasma proteins from a cryoprecipitatable blood plasma protein by precipitating the cryoprecipitatable protein, or washing the cryoprecipitatable protein with an aqueous solution comprising a non-polar polymeric material;
    (ii) lyophilising the cryoprecipitatable protein; and
    (iii) undertaking a viricidal heat treatment of the lyophilised cryoprecipitatable protein so as to be non-infective.

11. A process according to claim 10 wherein the cryoprecipitatable protein is fibronectin, Factor VIII or Factor XIII.

12. A process according to claim 10 wherein the cryoprecipitatable protein is fibrinogen.

13. A process according to claim 10 wherein the non-polar polymeric material used for washing is a polyethylene glycol.

14. A process according to claim 13 wherein the wash solution comprises 3 to 30% wt/vol of polyethylene glycol.

15. A process according to claim 10 wherein the aqueous wash solution is free of sugars.

16. A process according to claim 10 wherein washing is carried out at a temperature in the range 4° to 10° C.

17. A process according to claim 10 wherein the washing solution has a pH in the range 6.8 to 8.

18. A process according to claim 10 wherein the cryoprecipitatable protein prior to lyophilisation is formulated to include a carbohydrate and/or amino acid.

19. A process according to any of claims 10 to 18 wherein the lyophilised protein is heat treated at least at a severity of 80° C. for 72 hours.

20. A process according to claim 10 wherein the lyophilised protein is heat treated at least at a severity of 90° C. for 10 hours.

21. A process according to claim 10 wherein the heat treatment is a terminal heat treatment carried out as the last step of said process.

* * * * *